US008613711B2

(12) United States Patent
Babcock

(10) Patent No.: US 8,613,711 B2
(45) Date of Patent: Dec. 24, 2013

(54) STOOL SAMPLE COLLECTOR

(76) Inventor: Lee L. Babcock, Fairbanks, AK (US)

( * ) Notice: Subject to any disclaimer, the term of this patent is extended or adjusted under 35 U.S.C. 154(b) by 233 days.

(21) Appl. No.: 12/930,710

(22) Filed: Jan. 15, 2011

(65) Prior Publication Data
US 2011/0275954 A1 Nov. 10, 2011

Related U.S. Application Data

(60) Provisional application No. 61/330,979, filed on May 4, 2010.

(51) Int. Cl.
A61B 10/00 (2006.01)
A47K 11/00 (2006.01)
A61M 1/00 (2006.01)
A61F 13/15 (2006.01)
A61F 13/20 (2006.01)

(52) U.S. Cl.
USPC ............ 600/562; 4/144.2; 604/317; 604/322; 604/358

(58) Field of Classification Search
USPC .......... 600/562; 604/317–319, 322, 349, 403, 604/358; 4/661, 483–486; 206/438; 242/160.4; 436/66
See application file for complete search history.

(56) References Cited

U.S. PATENT DOCUMENTS

| 2,840,826 | A | * | 7/1958 | Ebbesen et al. ................... 4/661 |
| 3,571,817 | A | | 3/1971 | Gosnell |
| 3,588,921 | A | | 6/1971 | Nagel |
| 3,638,789 | A | * | 2/1972 | Tuszewski .................... 206/438 |
| 3,754,287 | A | | 8/1973 | Taylor |
| 4,101,279 | A | | 7/1978 | Aslam |
| 4,112,524 | A | | 9/1978 | Johansson |
| 4,309,782 | A | * | 1/1982 | Paulin .............................. 4/661 |
| 4,445,235 | A | * | 5/1984 | Slover et al. ................... 4/144.2 |
| 4,521,520 | A | * | 6/1985 | Jacke .............................. 436/66 |
| 4,935,969 | A | | 6/1990 | Farnsworth |
| 5,060,317 | A | | 10/1991 | Bertelsen |
| 5,337,426 | A | | 8/1994 | Matusewicz et al. |
| 5,463,782 | A | | 11/1995 | Carlson et al. |
| 6,351,857 | B2 | | 3/2002 | Slaon, III et al. |
| 6,358,477 | B1 | | 3/2002 | Webb et al. |
| 6,434,762 | B2 | | 8/2002 | Gordon |
| 6,640,355 | B1 | * | 11/2003 | Samide ............................. 4/661 |
| 7,204,443 | B2 | * | 4/2007 | Niki et al. .................. 242/160.4 |
| 2006/0179563 | A1 | * | 8/2006 | Kneese et al. ..................... 4/661 |
| 2007/0245486 | A1 | | 10/2007 | Battle et al. |
| 2008/0219885 | A1 | * | 9/2008 | Horstman ....................... 422/61 |
| 2011/0270125 | A1 | * | 11/2011 | Sonderholm et al. ......... 600/562 |

* cited by examiner

Primary Examiner — Sean Dougherty
Assistant Examiner — Devin Henson
(74) Attorney, Agent, or Firm — Anthony Claiborne

(57) ABSTRACT

A stool sample collector is comprised of a sheet of water-soluble material such as heavy-weight polyvinyl alcohol film, six to nine inches by 20 to 26 inches. In use, the strip is positioned across the toilet bowl against the bowl's back rim, the front edge of the strip drooping down to a few inches above the toilet water. The strip is affixed across the bowl by moistening at each end and pressing against the sides of the bowl. Positioning of the strip is facilitated by markings on the strip. Retention of stool samples is enhanced by dimples or riffles in the strip. After use, the strip may be removed and flushed in a domestic toilet.

3 Claims, 1 Drawing Sheet

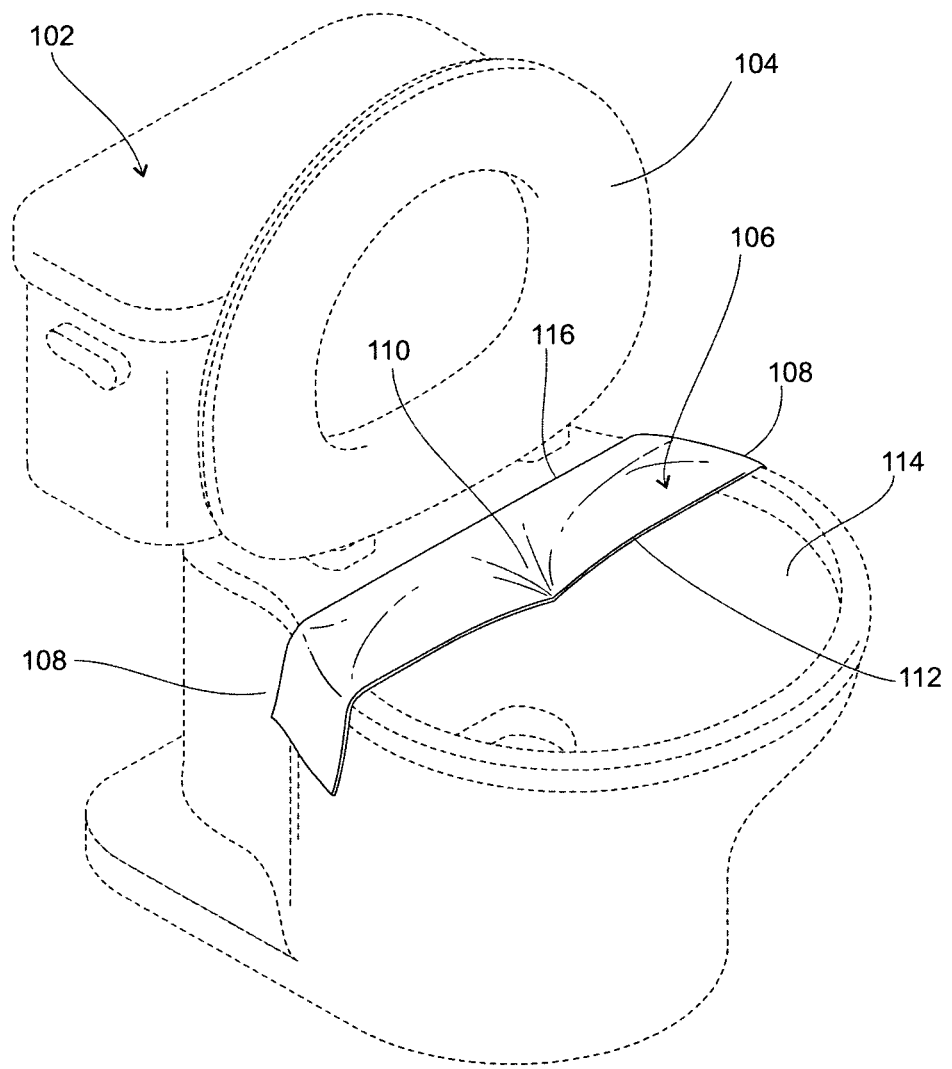

STOOL SAMPLE COLLECTOR

CROSS REFERENCE TO RELATED APPLICATION

This application claims priority from U.S. provisional application No. 61/330,979 filed May 4, 2010, entitled "For contamination free feces sample collection".

BACKGROUND OF THE INVENTION

1. Field of the Invention

This invention relates to an apparatus for stool sample collection and particularly to a stool sample collection device of simple construction that is flushable in the toilet along with domestic liquid waste.

2. Description of the Related Art

Medical service providers often require a patent to supply a stool sample for purposes of diagnosing the patient's medical condition. Usually, the patient herself must obtain the stool sample, typically by evacuating their bowels onto a device for collecting the sample. A number of such devices attach to a conventional toilet, hanging within the toilet below the patient's posterior and collecting stools from the patient as she defecates. Exemplary of such devices is that by Slover et al. (U.S. Pat. No. 4,445,235), which comprises a substantially impervious receptacle with a pair of side straps having an adhesive portion for contact adhesion to the top surface of a conventional toilet seat, the container being suspended below the toilet seat and above the surface of the water in the toilet, positioned to catch and retain a fecal specimen.

Because of the dimensions and position of the Slover device, a patient using the device must preferably use restraint in discharge of urine while defecating in order to avoid contaminating the stool sample and/or weakening the material comprising the device. A patient in a weakened medical condition may often find exercising such restraint difficult if not impossible.

While it is claimed that such devices may be flushed in the toilet when the sample has been taken, Slover's device is fabricated of a flexible water-resistant paper with an internal fiber reinforcement web. Experience has shown that, in fact, devices fabricated of such materials are not readily disposable in most domestic toilets and, while they occasionally flush, they often cause sewage plugging and backups in actual use. Further, the adhesive pads of the Slover device are often difficult to peel off the toilet sides after use and, even if the material comprising the device as a whole might otherwise flush down the toilet, the adhesive pads can inadvertently adhere to the inner passageways of the toilet itself or to sewer pipes connected to the toilet, thereby clogging the toilet or sewer pipes.

Another such device is described in U.S. Pat. No. 5,463, 782 to Carlson. Carlson's device is comprised of a single sheet of foldable material with at least three extensions and a cupping section formed at the intersection of the extensions. As with the device of Slover et al., Carlson's device is held in place by adhesive tabs adhering to the toilet rim at the ends of the device's extensions. Carlson states that his device is fabricated of light-weight, disposable sheet material such as tissue paper, fabrics or plastic. While some such devices are characterized as disposable or biodegradable, Carlson neither describes nor anticipates material that is actually generally flushable in a domestic toilet. Accordingly, Carlson's device has some of the same shortcomings as that of Slover: adhesive elements that are difficult to remove from the toilet after use and unsuitability for reliable disposal by flushing. While the Carlson device has a cupping section for restraining the specimen from inadvertently sliding off the device prior to the patient's obtaining a sample, the additional complexity of fabrication required to create the cupping section for Carlson's device is a drawback to this feature.

The related art contains many examples of disposable devices for feces collection that, like those of Slover et al. and Carlson, are comprised of paper collectors fabricated in some way to catch and retain feces samples. Many of these devices are of complex configurations difficult to manufacture. A number of these devices require the user to refrain from urination during use of the device. All of these devices require either adhesive or mechanical means of fixation on the toilet for use. And, while a domestic toilet may occasionally accommodate the disposal of some of these devices, none of the prior art devices are truly flushable by design.

What is needed is a device for collection of feces samples that is very simple in design for ease of manufacture. What is needed further is a device that may be releasably fixed to a toilet during use without the need for adhesives or mechanical fixation. What is needed further in such a device is a configuration allowing a user of either gender to urinate while defecating. What is needed yet further is such a device that is reliably flushable in a standard domestic toilet.

BRIEF SUMMARY OF THE INVENTION

The present invention is a device for the collection of stool samples, comprised of water-soluble sheet material. The device is configured as a strip of sufficient length to traverse the toilet bowl with some overhang and whose width is substantially less than the back-to front length of a toilet bowl. In use, the strip is affixed across the toilet bowl against the bowl's back rim, allowing the front edge of the strip to droop down into the bowl a few inches above the water in the bowl, leaving sufficient space open in the bowl in front of the strip for users of either gender to urinate directly into the water of the bowl. It is characteristic of the sheet material of the present invention that the strip may be affixed to the bowl at either side by moistening each end of the strip, positioning the strip against the back of the toilet as described above, then pressing the moistened ends of the strip against the outside of the bowl. In some embodiments, markings are provided on the device to assist the user in proper alignment when affixing the strip. Additionally, in some embodiments the sheet is further riffled or dimpled in order better to retain the stool sample.

BRIEF DESCRIPTION OF THE DRAWING

The foregoing features, as well as further objects, advantages, features and characteristics of the present invention, in addition to methods of operation, function of related elements of structure, and the combination of parts and economies of manufacture, will become apparent upon consideration of the following description and claims with reference to the accompanying drawing, which forms a part of this specification, wherein:

FIG. 1 depicts the present invention affixed to a toilet bowl, properly aligned to receive stool samples.

DETAILED DESCRIPTION OF THE INVENTION

The present invention is fabricated from water-soluble sheet material. Heavy-weight polyvinyl alcohol film, such as Ultra Solvy™ manufactured by Sulky of America, Inc. of Kennesaw, Ga., provides characteristics desired in preferred embodiments. While such material is completely water-soluble, it remains a semi-solid plastic sheet with strength and flexibility comparable to that of similar weight polyethylene film for the period of time required to collect a stool sample. Further, when moistened, the polyvinyl alcohol film adheres removably but firmly to the smooth porcelain surface of the toilet bowl. Yet further, when sampling is complete the device is easily removed from the toilet and, because such film is water-soluble, the spent material may be flushed in a domestic toilet without risk of clogging.

While any number of patterns and configurations of the sheet material may be employed for the present invention, FIG. 1 depicts a preferred embodiment comprising a rectangular strip of the material approximately 24 inches in length by 7⅞ inches in width. To prepare the invention for use, the seat 104 of toilet 102 is raised. The undersides of ends 108 of strip 106 are moistened with a wet sponge or cloth along a portion about 2 inches in length. If the stool sample collector is provided in the form of a kit, a suitably fashioned sponge may be included for this purpose. Strip 106 is aligned across the toilet bowl 114 with one side of the length of strip 106 against the back rim 116 of bowl 114, allowing the central portion 110 of the strip to droop into the bowl so that the leading edge 112 of strip 106 is roughly 2 inches above the water in bowl 114. With strip 106 so aligned, the moistened ends 108 are then pressed against the sides of bowl 114, where the natural adhesion of the moistened strip material will hold the device in place for the length of time required to produce the stool sample. With the device in place, the toilet seat 104 is lowered and the user of either gender may then empty their bladder in the open portion of the toilet bowl 114 forward of leading edge 112 of strip 106. Subsequently, the user deposits feces onto strip 106. After defecating, the user gathers feces retained on strip 106 into a sample container in a manner that will be familiar to those in the art. After the feces sample is gathered, the user lifts ends 108 of strip 106 from the rim of toilet 102, deposits used strip 106 in toilet bowl 114 and flushes toilet 102.

Embodiments of the present invention may further provide imprinted markings on strip 106 to guide the user in aligning strip 106 as described above on toilet 102. As is well known to those in the art, there are two standard configurations of toilet: round and elongated. Standard dimensions for round toilets are about 24.5 inches by 19.5 inches by 26 inches. Standard dimensions for elongated toilets are about 30.5 inches by 19.5 inches by 26 inches. In either case, since the standard width is about 19.5 inches, marks applied to strip 106 to align the strip along the width of toilet bowl 114 will enable the user to affix strip 106 to toilet 102 to provide the desired amount of droop for central portion 110 for any standard toilet.

Embodiments of the present invention may enhance the ability of the central portion 110 of strip 106 to retain feces deposited thereon by fabricating strip 106 with dimpling or transverse riffles to retain the feces against downward gradient along central portion 110 of strip 106 from the back rim 116 of bowl 114 to leading edge 112 of strip 106. Dimpling can comprise raised portions of film $\frac{1}{32}$ of an inch above the film surface on ¼ inch centers. Riffles can be ¼ inch in width running lengthwise along the central portion 110 of strip 106. Film with such riffling or dimpling can be manufactured by means of rollers or other manufacturing apparatus configured for such purpose, as will be understood by those of skill in the art.

Although the detailed descriptions above contain many specifics, these should not be construed as limiting the scope of the invention but as merely providing illustrations of some of the presently preferred embodiments of this invention. Various other embodiments and ramifications are possible within its scope, a number of which are discussed in general terms above.

While the invention has been described with a certain degree of particularity, it should be recognized that elements thereof may be altered by persons skilled in the art without departing from the spirit and scope of the invention. Accordingly, the present invention is not intended to be limited to the specific forms set forth herein, but on the contrary, it is intended to cover such alternatives, modifications and equivalents as can be reasonably included within the scope of the invention. The invention is limited only by the following claims and their equivalents.

I claim:

1. A stool sample collector, consisting of a flexible strip of heavy-weight polyvinyl alcohol film, approximately 24 inches in length by approximately 7⅞ inches in width, the strip marked for alignment with a toilet bowl, the strip further fashioned with at least one of riffles and dimples in the film.

2. A kit for collecting stool samples, comprising a sample collector consisting of a strip of flexible heavy-weight polyvinyl alcohol film approximately 24 inches in length by approximately 7⅞ inches in width marked for alignment with a toilet bowl, the strip further fashioned with at least one of riffles and dimples in the film, and a sponge suitable for moistening a portion of the strip.

3. A method of collecting stool samples employing a flexible rectangular strip consisting of polyvinyl alcohol film having two widthwise edges of approximately 7⅞ inches and having first and second lengthwise edges of approximately 24 inches, and a toilet having a bowl with a front rim, a back rim, and outer sides, the method comprising:
   moistening the terminal 2 inches of each widthwise edge of the strip;
   draping the strip lengthwise across the toilet bowl while aligning the first lengthwise edge of the strip with the back rim of the toilet bowl while the second lengthwise edge of the strip faces the front rim of the toilet bowl;
   providing enough slack in the strip so that the second lengthwise edge droops to a height of approximately two inches above the water in the bowl; and
   pressing the moistened widthwise edges of the strip against the outer sides of the toilet bowl to cause the strip to adhere to the toilet bowl.

* * * * *